United States Patent [19]
Karim

[11] 4,005,221
[45] Jan. 25, 1977

[54] USE OF PROSTAGLANDINS TO INDUCE MENSTRUATION
[76] Inventor: Sultanali M. M. Karim, 82 Eng Neo Ave., Singapore 11
[22] Filed: Sept. 29, 1975
[21] Appl. No.: 617,888

Related U.S. Application Data

[63] Continuation of Ser. No. 457,006, April 1, 1974, abandoned, which is a continuation of Ser. No. 151,898, June 10, 1971, abandoned, which is a continuation-in-part of Ser. No. 73,670, Sept. 18, 1970, abandoned.

[52] U.S. Cl. .................................. 424/317; 424/305
[51] Int. Cl.$^2$ ............... A61K 31/215; A61K 31/19

[58] Field of Search ........................... 424/305, 317

[56] References Cited
OTHER PUBLICATIONS

Farley Manning Associates Inc. News Release Dec. 29, 1968–six pages.

*Primary Examiner*—Sam Rosen

[57] ABSTRACT

Menstruation in non-pregnant women is induced near the due date of menses by intravaginal administration of prostaglandins of the PGE and PGF types.

8 Claims, No Drawings

USE OF PROSTAGLANDINS TO INDUCE MENSTRUATION

CROSS REFERENCE TO RELATED APPLICATION

This application is a continuation of copending application Ser. No. 457,006, filed Apr. 1, 1974, now abandoned, which is a continuation of copending application Ser. No. 151,898, filed June 10, 1971, now abandoned, which is a continuation-in-part of copending application Ser. No. 73,670, filed Sept. 18, 1970, now abandoned.

BACKGROUND OF THE INVENTION

A crude mixture, called prostaglandin was reported by Goldblatt, Chem. Ind. London 52,1056 (1933); J. Physiol. London 84, 208 (1935) and von Euler, Arch. Exp. Path., Pharm. Abs. 175,78 (1934); 181 (1936); J. Physiol. 72,74 (1931); 81,102 (1934); 84,21 (1935); 88, 213 (1936); and Klin. Wschr. 14, 1182 (1935). Since then isolation, purification, preparation of derivatives and biological studies of the prostaglandins have continued. For example, microbiological conversions of unsaturated fatty acids with mammalian glandular tissue are described in U.S. Pat. Nos. 3,290,226 and 3,296,091. In U.S. Pat. No. 3,290,226 PGE compounds are described including $PGE_1$, $PGE_2$, and $PGE_3$. The PGE series is characterized by the presence of the keto group at the 9-position in the cyclopentane ring. More recently, Ramwell et al, "Prostaglandins" in Progress in the Chemistry of Fats and Other Lipids, Vol. 9, edited by R. Holman, pp. 231–273, Pergamon Press, Oxford, 1968 refer to prostaglandin $PGE_1$ as $11\alpha,15(S)$-dihydroxy-9-oxo-13-trans-prostenoic acid, $PGE_2$ as $11\alpha,15(S)$-dihydroxy-9-oxo-5-cis,13-trans-prostadienoic acid and $PGE_3$ as $11\alpha,15(S)$-dihydroxy-9-oxo-5-cis,13-trans, 17-cis-prostatrienoic acid. $PGE_1$ is converted to dihydro-$PHE_1$ by catalytic hydrogenation as described in Belgian Pat. No. 685,516. Following the prostanoic acid nomenclature, dihydro-PGE: is named as $11\alpha,15(S)$-dihydroxy-9-oxoprostanoic acid.

Pharmaceutically acceptable salts, for example, those of alkali metals and alkaline earth bases, such as the sodium, potassium, calcium and magnesium salts; those of ammonia or a basic amine such as mono-, di-, and triethyl amines, benzylamines, heterocyclic amines such as piperidine and morpholine, and amines containing water-solubilizing or hydrophilic groups such as triethanolamine, tris(hydroxymethyl)aminomethane, and phenylmonoethanolamine are described in U.S. Pat. No. 3,296,091. Carboxylate esters, wherein the esterfying radical has 1 to 8 carbon atoms inclusive, especially 1 to 4 carbon atoms, inclusive, illustratively the methyl, ethyl, butyl, cyclohexyl and octyl esters are formed by the usual methods, e.g., reaction with diazomethane or similar diazohydrocarbons as in U.S. Pat. No. 3,296,091. Acylates of lower alkanoic acids of 1 to 8 carbon atoms, inclusive, are prepared in the usual manner by reaction of the respective prostaglandin acids with the appropriate acid anhydride or acid halide, e.g., those of formic, acetic, propionic, butyric, isobutyric, valeric, caproic, caprylic and the like acids, as in Great Britain Pat. Spec. No. 1,040,544. Among these the acylates wherein the acyl radical has 2 to 4 carbon atoms are preferred, especially the acetate.

Biological studies of the prostaglandins, for example, actions on smooth muscle, reproductive system, nervous system, cardiovascular system, and relationship to lipid and carbohydrate metabolism, and miscellaneous effects are summarized by Bergstrom et al; "The Prostaglandins: A Family of Biologically Active Lipids," Pharmacological Reviews, Vol. 20, No. 1, p. 1 et sequitur, March, 1968, the Williams and Wilkins Company. Further biological studies include the effect of $PGF_2$ on isolated strips of human pregnant and non-pregnant myometrium in vitro. Bygdeman (1964) Acta. Physiol. Scand. 63, (suppl. 242), 1; Pickles and Hall (1963) J. Reprod. Fert. 6, 315 and Sandberg et al. (1965) Acta. Obstet, Gynec. Scand, 44, 585. Also Karim, S.M.M. (1966) J. Obstet, Gynaec. Brit. Cwlth. 73, 903 and Karim and Devlin (1967) ibid., 230 have shown that $PGF_2 \alpha$ is present in human amniotic fluid obtained during labor. Further, Karim, British Med. J. 4, 618 (1968) has shown that $PGF_2 \alpha$ appears in the maternal venous blood in variable amounts during labor.

It is against this background that the present invention has been conceived and embodied.

BRIEF SUMMARY OF THE INVENTION

This invention relates to the use of certain prostaglandins for benefically and advantageously inducing menstruation in sexually-mature, non-pregnant, non-menopausal human females. More specifically the prostaglandin active ingredient is administered intravaginally in a dosage unit form of a pharmaceutical for supplying to the subject female a nontoxic, effective amount of said ingredient for inducing the menstruation.

The active prostaglandin ingredient is a compound selected from the group consisting of $PGE_1$, $PGE_2$, $PGE_3$, dihydro-$PGE_1$, $PGF_{1\alpha}$, $PGF_{2\alpha}$, $PGF_{3\alpha}$, dihydro-$PGF_{1\alpha}$, $PGF_{1\beta}$, $PGF_{2\beta}$, $PGF_{3\beta}$, dihydro-$PGF_1\beta$, pharmaceutically acceptable salts thereof, acylates thereof wherein the acyl radical is that of a lower alkanoic acid having 1 to 8 carbon atoms, inclusive, and carboxylate esters thereof wherein the esterfying radical has 1 to 8 carbon atoms, inclusive. These are to be construed as including the optically active compounds of the natural configuration and the racemic compounds. These compounds are known in the art or are available by methods known in the art. For the racemic compounds, see, for example J. Am. Chem. Soc., 91:5364 (1969); J. Am. Chem. Soc. 91:5372 (1969); Chem. Communications, 302 (1969); and Chemical Communications, 602 (1970).

DESCRIPTION OF THE PREFERRED EMBODIMENTS

It is especially advantageous to administer dosage unit forms for ease and economy of administration and uniformity of dosage. Dosage unit form as used in the specification and claims herein refers to physically discrete units suitable as unitary dosages for animal and human subjects, each unit containing a predetermined quantity of active material calculated to produce the desired biological effect in association with the required pharmaceutical means.

Effectiveness of the mode of administration intravaginally is dependent on providing to the subject female a nontoxic effective amount of the prostaglandin active ingredient for inducing menstruation. In harmony with the concept of so administering to the subject such an effective amount of the prostaglandin ingredient various dosage unit forms are operable. Illustratively, the dosage unit forms include a tampon, a sprayable liquid preparation, a suppository, a tablet, a liquid preparation adapted to form an aerosol, a solid preparation adapted for insufflation such as a powder, a liquid preparation adapted for instillation and similar preparations suited for intravaginal administration. These dosage unit forms are made up by preparative techniques available in the art.

The amount of the prostaglandin to be administered varies with the age, weight and condition of the subject to be treated. Illustratively, a single dose of 20 mg. of prostaglandin $E_2$ will suffice for some subjects. Other subjects will require a repeat of this dosage after about 4 hours. Some subjects will require yet a third dosage usually on the next day. In the case of prostaglandin $F_2 \alpha$ 50 mg. will suffice for some subjects, repeated as required at an interval of about 4 hours, with a third dosage being given in usually non-sensitive subjects. Generally the overall effective range of the prostaglandin active ingredient including the salts, acylates and esters is from about 0.1 mg/kilo to about 6 mg/kilo. The dosage regimen embodying an effective amount to induce menstruation is given during a span of time beginning about 4 days before and ending about 6 days after expected day of onset of menses. Regularity of menses is thereby brought about with unexpected benefits especially in subjects with varying onset of menses in the absence of treatment according to the present inventive process. Illustratively vaginally-administered tablets are prepared by applying to a 2 gm. lactose tablet sufficient ethyl alcohol solution of prostaglandin $E_2$ or $F_2 \alpha$ to provide a tablet containing 20 mg of the former or 50 mg of the latter. A convenient ethyl alcohol solution contains 250 mg of the active ingredient per milliliter. Such tablets are placed in the posterior fornix of the vagina. Vaginally-applied dosage unit forms other than tablets are prepared with reference to the physical characteristics, especially solubility, of the particular prostaglandin to be administered intravaginally. A pregnancy test, preferably of the immunological type is used to check the condition of the patient before treatment. Such test is also a useful check after menses ensues.

In one female, vaginal administration is begun two days after missed menses. Prior to treatment, a pregnancy test is negative. The tablet dosage form contains 20 mg of prostaglandin $PGE_2$ and two intravaginal administrations, each one tablet, suffice to produce onset of bleeding 3 hours after the second administration. A pregnancy test 1 week later is negative. In another female subject the table dosage form contains 50 mg of prostaglandin $PGF_2 \alpha$. Similar results are obtained with two tablets, with onset of bleeding being 4 hours after the second dose. Again both prior and subsequent tests for pregnancy are negative. In a third subject treatment is begun 6 days after missed menses. The tablet dosage form contains 20 mg. of prostaglandin $PGE_2$ and two intravaginal doses are given. Bleeding begins 6 hours after the second dose. In yet another female bleeding did not follow a third dose of 20 mg prostaglandin $PGE_2$ on a second day. In this case although the initial test for pregnancy is negative the after-one-week test is positive showing an initial false negative. Similar results are obtained in other patients using other dosage forms such as a solution, a suspension, an aerosol, a powder, especially a powder form of a water-soluble salt.

I claim:

1. A method of inducing menstruation in a sexually-mature, nonpregnant, nonmenopausal human female which consists essentially of administering intravaginally to a said female within a period of from about 4 days before to about 6 days after said female's expected day of onset of menses a vaginal dosage unit form supplying an effective, nontoxic amount for inducing the menstruation of a prostaglandin selected from the group consisting of $PGE_1$, $PGE_2$, $PGE_3$, dihydro-$PGE_1$, $PGF_1 \alpha$, $PGF_2 \alpha$, $PGF_3 \alpha$, dihydro-$PGF_1 \alpha$, $PGF_1 \beta$, $PGF_2 \beta$, $PGF_3 \beta$, dihydro-$PGF_1 \beta$, pharmaceutically acceptable salts thereof, acylates thereof wherein the acyl radical is that of a lower alkanoic acid having 1 to 8 carbon atoms, inclusive, and carboxylate esters thereof wherein the esterfying radical has 1 to 8 carbon atoms, inclusive.

2. The method of claim 1 wherein the effective nontoxic amount for inducing the menstruation is within the range of about 0.1 mg per kilo to about 6 mg per kilo of body weight of said female.

3. The method of claim 1 wherein the prostaglandin is $PGE_2$ or a pharmaceutically acceptable salt thereof.

4. The method of claim 1 wherein the prostaglandin is $PGF_2 \alpha$ or a pharmaceutically acceptable salt thereof.

5. The method of claim 2 wherein the prostaglandin is $PGE_2$ or a pharmaceutically acceptable salt thereof.

6. The method of claim 2 wherein the prostaglandin is $PGF_2 \alpha$ or a pharmaceutically acceptable salt thereof.

7. The method of claim 3 wherein the total amount of $PGE_2$ or salt thereof is 40 mg.

8. The method of claim 4 wherein the total amount of $PGF_2 \alpha$ or salt thereof is 100 mg.

* * * * *